United States Patent [19]

Meseke et al.

[11] 4,121,755
[45] Oct. 24, 1978

[54] DISPOSABLE COLLECTING CONTAINER FOR SMALL USED ARTICLES AND WASTE

[75] Inventors: Curt Th. Meseke, Leer, Ostfriesland; Winfried Winkler, Aachen, both of Fed. Rep. of Germany

[73] Assignee: Hammer-Lit GmbH, Leer, Ostfriesland, Fed. Rep. of Germany

[21] Appl. No.: 814,426

[22] Filed: Jul. 11, 1977

[30] Foreign Application Priority Data

Jul. 10, 1976 [DE] Fed. Rep. of Germany ... 7621822[U]
Jul. 5, 1977 [DE] Fed. Rep. of Germany ....... 2720591

[51] Int. Cl.² .......................... B65D 5/10; B65D 81/00
[52] U.S. Cl. ........................................ 229/38; 206/366; 229/39 R
[58] Field of Search .................... 229/38, 39, 41 R, 44; 206/63.5, 494, 365, 366

[56] References Cited

U.S. PATENT DOCUMENTS

| | | | |
|---|---|---|---|
| 1,502,606 | 7/1924 | Whelan | 229/38 X |
| 1,603,024 | 10/1926 | Childs | 229/38 X |
| 2,677,494 | 5/1954 | Buttery | 229/39 R |
| 2,890,791 | 6/1959 | Wenzel | 206/494 |
| 3,033,362 | 5/1962 | Marcalus | 206/494 |
| 3,089,633 | 5/1963 | Renshaw | 229/38 |
| 3,226,007 | 12/1965 | Thies et al. | 206/365 X |
| 3,374,937 | 3/1968 | Wilson | 229/39 R |
| 3,481,454 | 12/1969 | King | 229/38 X |
| 3,494,536 | 2/1970 | Henry | 229/39 R |

*Primary Examiner*—Davis T. Moorhead
*Attorney, Agent, or Firm*—Walter Becker

[57] ABSTRACT

A disposable collecting container of cardboard or synthetic material for used small articles and waste, especially for medical articles, which includes a substantially double layer blank which is foldable into an octagonal box. The wall which in folded-up condition of the box forms the upper longitudinal horizontal wall of the container is provided with a filling opening. The inlet opening is formed by wall sections and is adapted to be closed by yieldingly resiliently moving into the interior of the container.

12 Claims, 13 Drawing Figures

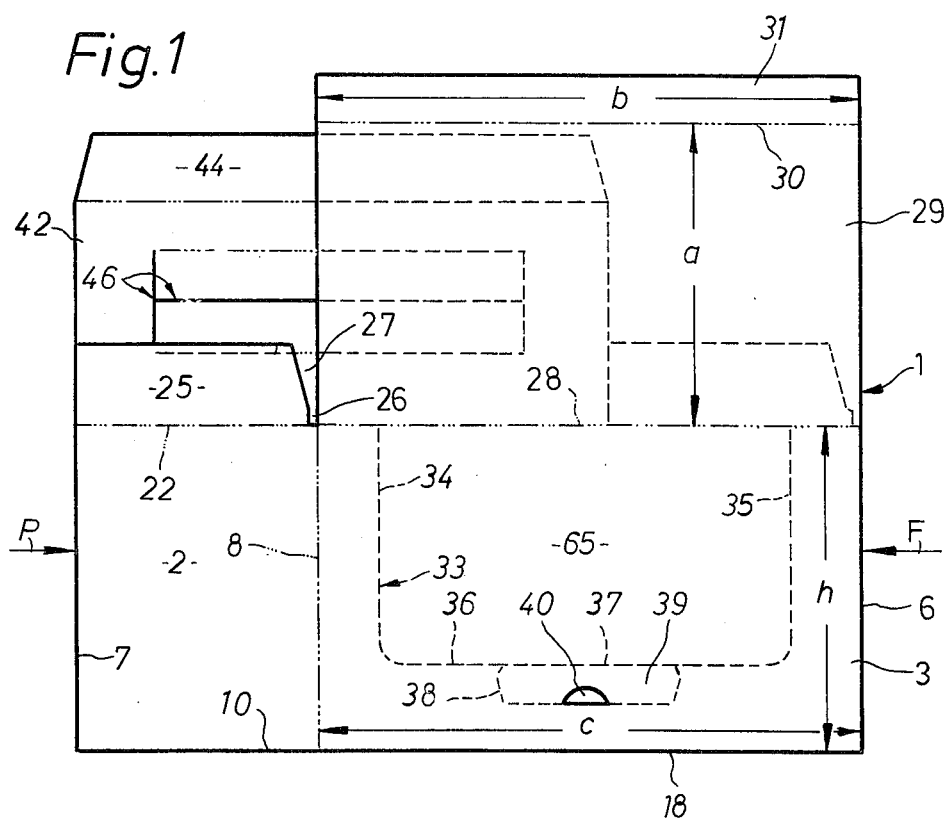
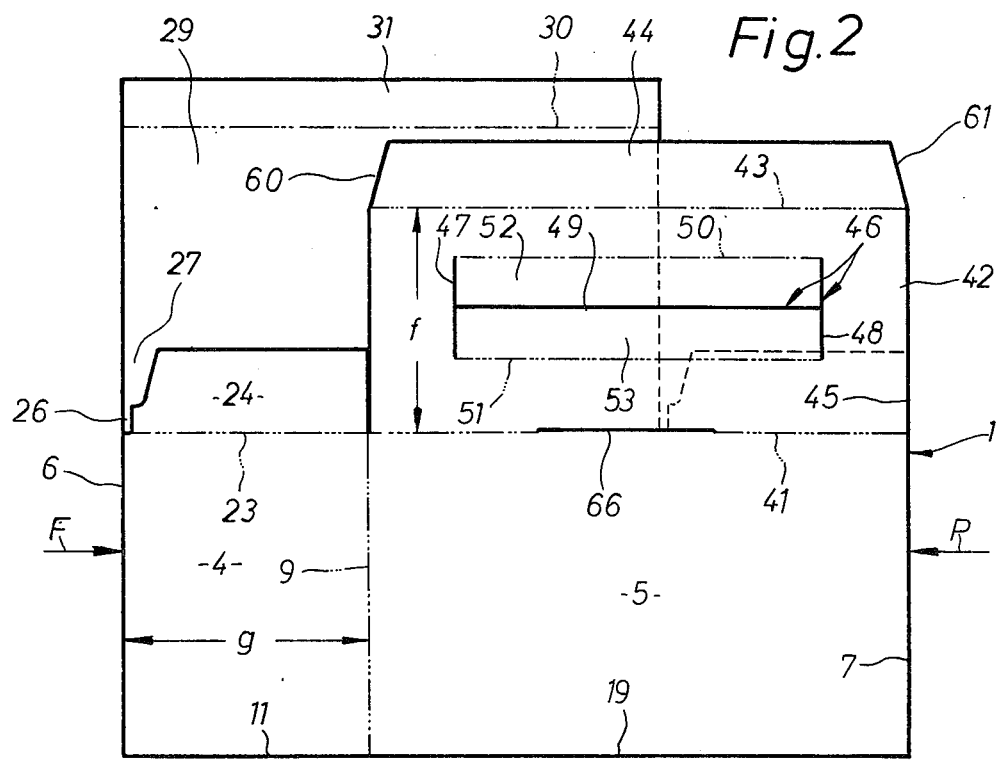

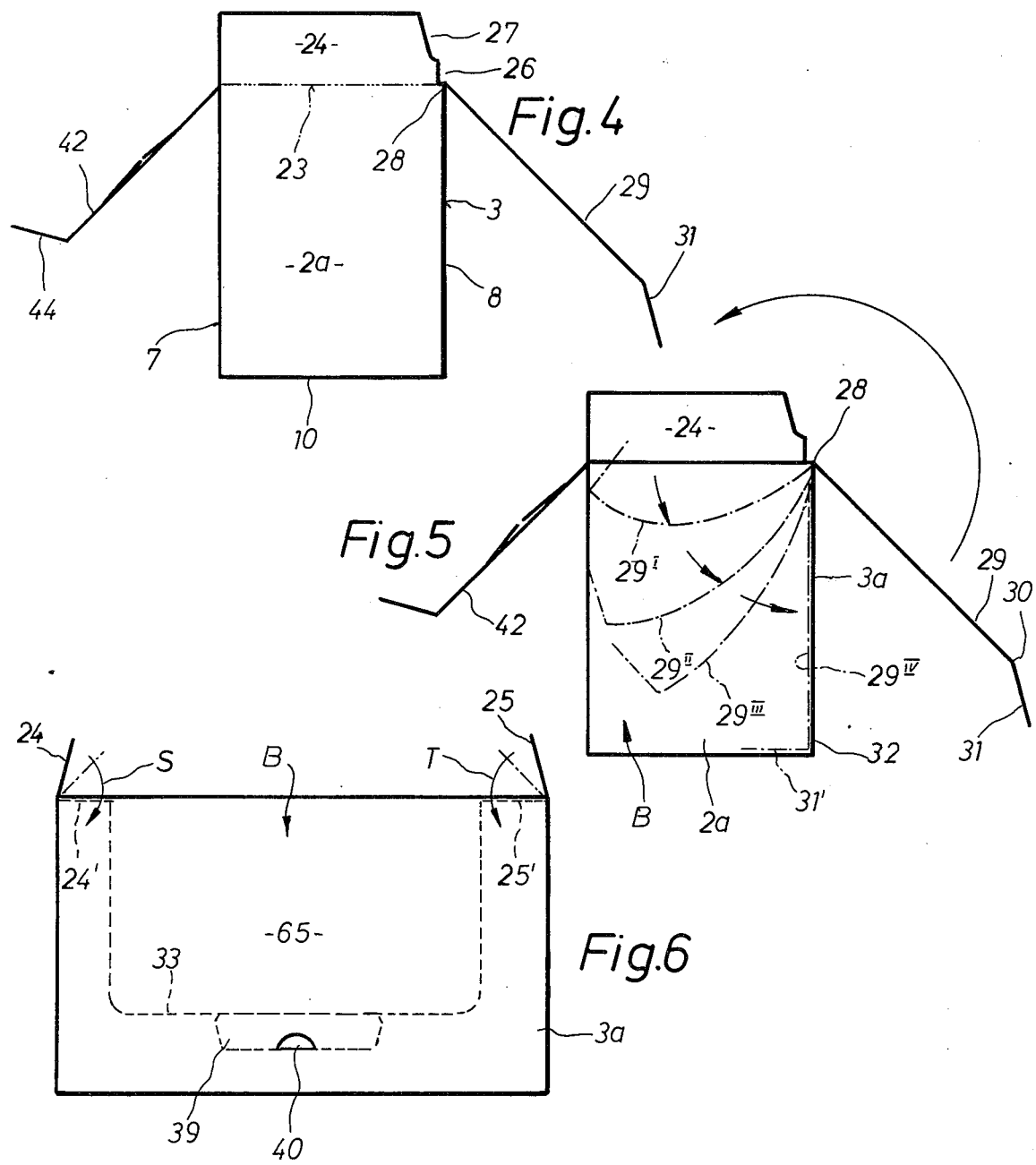

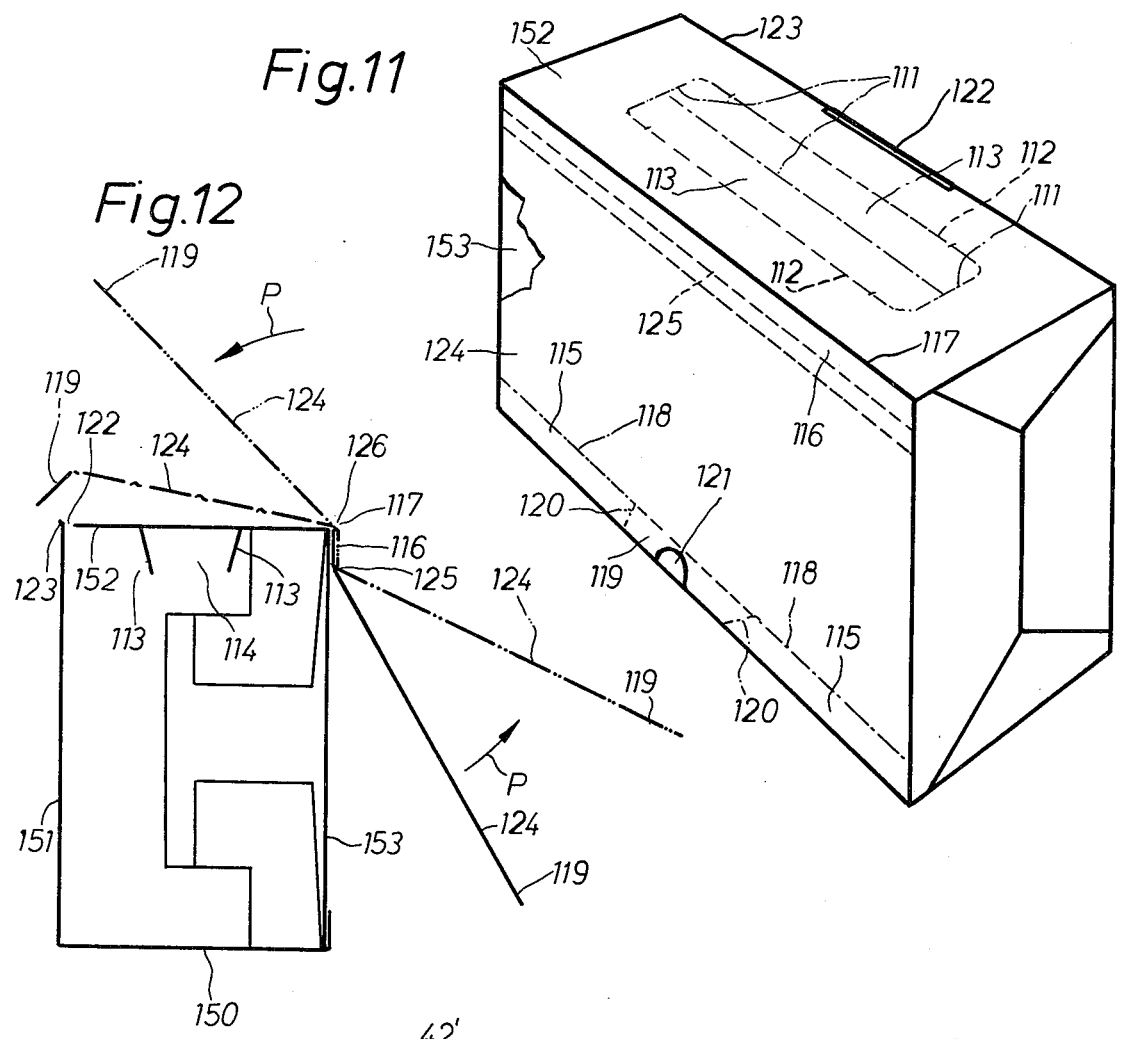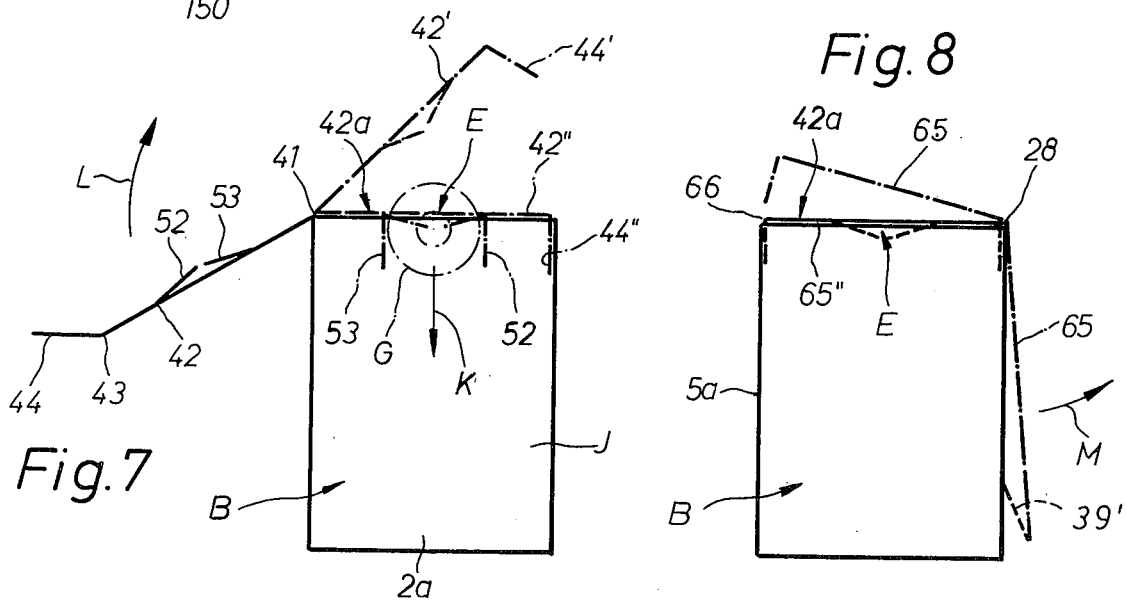

DISPOSABLE COLLECTING CONTAINER FOR SMALL USED ARTICLES AND WASTE

The present invention relates to a disposable collecting container, especially of cardboard or synthetic material, for used small articles and waste, particularly for medical articles which container is to be made from a substantially double-layer blank, foldable into an octagonal box. Cartons for cookies and other food are known which consist of a substantially double-layer blank which is foldable into an octagonal box, while the container bottom is formed by extensions of the container side walls which extensions are foldable into the bottom plane, and in which a cover is formed by an extension of one of the side walls which last mentioned extension extends above the upper container edge.

It is an object of the present invention to improve and further develop the above-mentioned heretofore containers so as to create a disposable collecting container for small articles and waste which container can in a minimum of time and without technical auxiliary means such as brackets or the like, by simple hand operations be folded from its substantially two-layered transport, storage or non-use condition to be folded into usable condition.

It is a further object of the invention to provide a container as set forth in the preceding paragraph in which the container opening is so designed that the insertion of the used articles and waste can easily be effected while the dropping-out of such articles and waste, for instance if the container should tilt over, can be prevented as well as the withdrawal of the used articles.

It is still another object of this invention so to design the container that after having been completely filled it can be safely closed so that for instance when using the container in medical establishments, needles, scalpels, syringes and the like cannot accidentally drop out of the container, and also pointed, sharp and contaminated parts of such articles cannot project from the container opening and cause damage.

These and other objects and advantages of the invention will appear more clearly from the following specification in connection with the accompanying drawings, in which:

FIGS. 1 and 2 respectively show the two sides of the blank of a first embodiment of a container according to the invention, occupying its substantially two-layer, folded-together starting position.

FIG. 3 shows the bottom of the container as folded out of the blank according to FIGS. 1 and 2.

FIG. 4 represents a view of one transverse wall of the folded-out container with the upper lateral wall extensions not yet folded inwardly.

FIG. 5 shows the folding-in of the double wall into the interior of the container.

FIG. 6 is a view of one side wall of the folded-up container with perforation.

FIG. 7 illustrates the folding-in of the upper side wall extension of the filling slots in its position of use.

FIG. 8 shows the closing of the inlet slot in the upper container wall, by means of the closure flap.

FIG. 11 is an isometric view of the closed container of FIG. 9.

FIG. 12 is a vertical cross sectional view of the container of FIG. 11.

Figure 9:
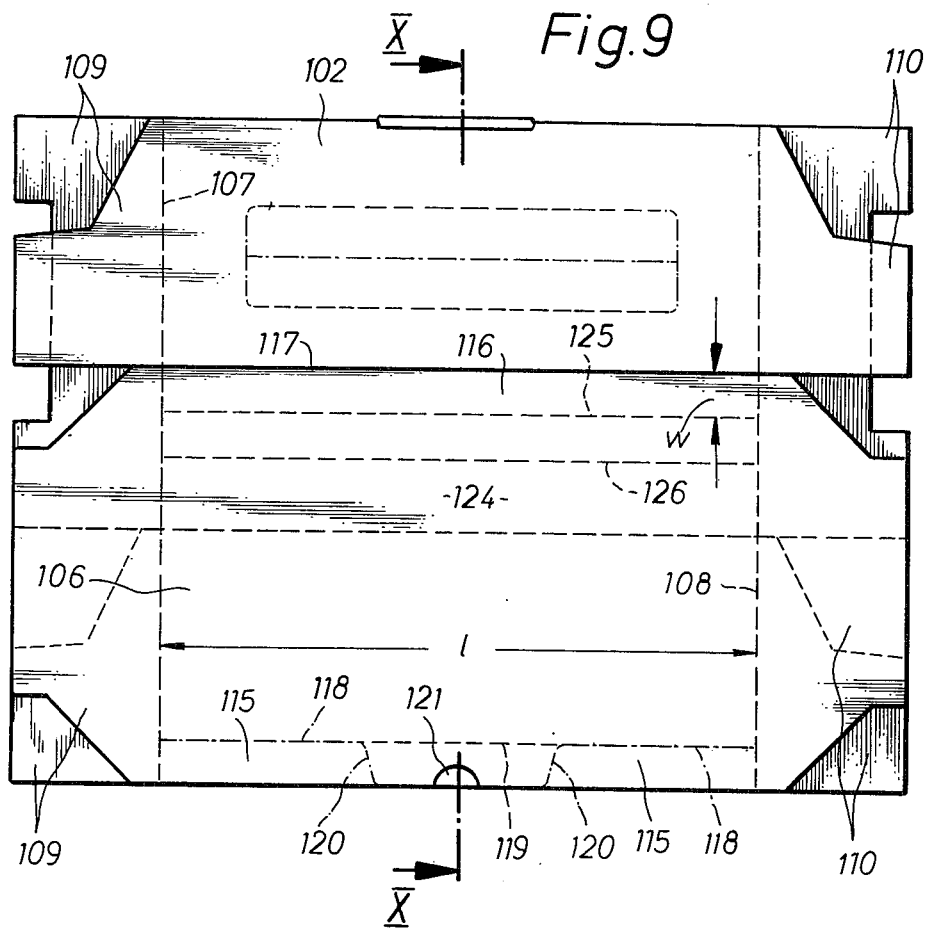
FIG. 9 illustrates the blank of a second embodiment, likewise in its substantially two-layer folded-together starting position.

The collecting container according to the invention is characterized primarily in that the wall which in folded-up condition of the container forms the upper horizontal longitudinal container wall is provided with a container opening formed by wall parts and adapted to be closed by flaps which are resiliently yieldably movable into the interior of the container.

For purposes of obtaining a complete closure after the container has been filled, one of the container side walls comprises two layers of which the outer layer is by at least one section as closure flap for the container opening pivotable about a longitudinal axis onto the upper longitudinal container wall.

According to a further advantageous development of the present invention, the closure flap which is pivotable onto the upper longitudinal container wall has a width which corresponds to the width or nearly the width of the longitudinal wall, and is equipped with an insert tongue adapted to be inserted into a corresponding slot in the upper longitudinal container wall.

Preferably, the closure flap is at its lower rim confined by a perforation adapted to be torn open, through which said closure flap is connected to a non-tiltable residual section of the outer longitudinal wall layer, while the perforation extends at a distance from and above the lower rim of the container side wall.

The container itself may be produced in various manners. Thus, the container bottom may be formed by foldable extensions of the container side walls which extensions are foldable into the bottom plane. The container cover which represents the upper longitudinal wall consists of an extension projecting beyond the upper longitudinal container edge, and the inner one of the two layers of one side wall may likewise be formed by an extension which is pivotable about the upper container rim into the interior of the container. In this connection, the tiltable longitudinal rim extension which is pivotable into the interior of the container may have the length and height of the container and may at its lower end be provided with a strip resting on the container bottom.

According to a modification of the container, the transverse walls of the container, which walls are foldable into the plane of said transverse walls, partially overlap each other in their position. These two layers of one side wall are interconnected at their upper and lower rim, and in upward and downward direction the adjacent respective rims of said interconnected regions are formed by extensions of the longitudinal walls which extensions are foldable into the plane of said walls; said extensions of the longitudinal walls partially overlap each other and hold each other in position. Furthermore, the two layers of one side wall are interconnected at their upper and lower rim, and the adjacent rims of said interconnected regions limit the closure flap in upward and downward direction. In this connection, the blank of the container consists of substantially rectangular cardboard or synthetic material which is folded at four parallel longitudinal lines and the distance of which corresponds to the width of the longitudinal walls of the container to be formed. The two longitudinal end sections of the blank overlap each other in the direction of the width of the two-layer container side wall.

According to a further embodiment of this invention, the two layers of one container side wall are at their upper and lower rim in sections of from 8-30mm widths partially glued to each other, while the longitudinal gluing region has a width equalling the width of the non-glued insertion tongue of the closure flap, the lateral rim of which is connected by means of an extension of the tearable perforation to the adjacent glued region. The upper rim of the closure flap may be provided with a folding line the width of which equals the width of the upper gluing region and on which the closure flap is tiltable over the insertion opening.

Preferably, the insertion opening which extends over a portion of the container length together with its flaps is formed by an I-shaped cut extending symmetrically with regard to the rims of the upper longitudinal container wall, one longitudinal flap rim remaining foldably connected to the container wall.

Referring now to the drawings in detail, the container according to the present invention is formed from a blank 1, one side wall of which namely the one which faces the observer of FIG. 1, comprises the blank section 2 which forms one transverse wall of the container to be folded up. The blank section 3 of blank 1 forms one side wall of the container. The blank 1 furthermore comprises the blank section 4 which represents the second container transverse wall, while a blank section 5 of blank 1 forms the second container side wall.

The blank sections 2 and 3 of the blank 1 are located in a common plane parallel to the plane in which the blank sections 4 and 5 are located. The edge 6 of the blank section 3 represents a bend by 180° and forms the outer confinement of the blank section 4, whereas the edge 7 of blank section 2 is folded by 180° and confines the blank section 5.

The sections 2, 3 and 4, 5 respectively have a folding line 8, 9 which together with the edges 6, 7 form the four vertical transverse edges of the folded-up container.

The two sections 2, 4 of the blank 1 comprise triangular sections 12, 13 (FIG. 3) which are adjacent the lower folding edges 10, 11 of sections 2, 4, and which in the substantially double-layer starting position engage the inner side of the sections 2, 4.

Separated from each other by a folding line 14, 15 the sections 12, 13 merge with the further sections 16, 17 which represent extensions (FIG. 3) that are folded about the edges 18, 19 of sections 3, 4 which edges represent the lower longitudinal container edges. In the starting position of blank 1, the sections 16, 17 engage the inner side of the sections 3, 5. The two sections 16, 17 furthermore comprise tongue-shaped extensions 20, 21 which extend below the respective adjacent sections 16 or 17 and the two triangular sections 12, 13 as is indicated in FIG. 3 by dot-dash lines.

For purposes of placing the bottom of the container in its proper position, it is merely necessary to exert a pressure upon the edges 6, 7 of the blank 1 in the direction of the arrows F, P in FIGS. 1 and 2 whereby the sections 12, 13 and 16, 17 are lifted off the inner side of sections 2-5 and occupy a position which is at a right angle to said sections 2-5, in other words form the bottom.

The sections 2, 4 of the blank 1 are provided with upper extensions 24, 25 comprising lateral cut-outs 26, 27 (FIGS. 1, 2 and 4), said upper extensions 24, 25 being foldable about the upper folding edges 22, 23 in the direction of the arrows S, T in FIG. 6.

An extension 29 of section 3 (FIGS. 1-5) is foldable about the upper longitudinal edge 28 of section 3 parallel to the bottom of the container. The length $b$ of said extension 29 approximately corresponds to the length $c$ of section 3. A tongue-shaped strip 31 is foldable about the folding line 30 which is spaced from edge 28 by a distance $a$ which in its turn corresponds to the height $h$ of section 3 and thus of the container. As shown in FIG. 5, the extension 29 can be tilted about the edge 28 into the intermediate positions $29'$, $29''$, and $29'''$ so that the extension 29 occupies the position $29^{IV}$, and the tongue-shaped strip 31 takes up the position $31'$. In this connection, the extension 29 in its position $29^{IV}$ forms a double wall with regard to the side wall of the container formed by section 3. The flap-like strip 31 rests on the bottom of the container (FIG. 5) which is formed by the sections 12, 13, 16 and 17 so that no material to be filled into said container can be placed in the intermediate space between the extension 29 and the position $29^{IV}$ of the latter on the one hand and the section 3 on the other hand, which means one longitudinal side wall of the container.

The section 3 of the blank 1 comprises a horse-shoe-shaped perforation 33 (FIG. 1) with the two regions 34, 35 which are located in spaced relationship to the edge 6 and the folding line 8 which regions are adjacent to one each 28 forming one upper longitudinal container each. The perforation 33 furthermore comprises an intermediate section 38 which has a folding line 37 at its central portion. A further perforation 38 starts at the ends of this folding line 37, said perforation 8 embracing a tongue 39 with a semi-circular cutout 40.

In FIG. 7 an extension 42 is foldable about the upper edge 41 of section 5 through the position $42'$ into the position $42''$. As a result thereof, the folded-up container is closed by the extension 42. A strip 44 is likewise foldable about the folding edge 43 of the extension 42. The width $f$ of the extension 42 corresponds to the width $g$ of the two parts 2 and 4, whereas the length of the extension 42 corresponds to the length $c$ of the two sections 3, 4 and thus to the length of the container.

The extension 42 which forms the upper container wall, comprises, symmetrically with regard to the longitudinal and transverse edges 41, 42, an I-shaped cut 46 with the two parallel sections 47, 48 and the web-like connecting section 49. The ends of the sections 47, 48 are in pairs interconnected by the folding lines 50, 51 as a result of which the flaps or tongues 52, 53 are formed.

The length and the spacing of the sections 47, 48 of the cut 46, and thereby the opening of the extension 42 which opening is closable by the flaps or tongues 52, 53. The extension 42 which forms the cover of the container, corresponds to an article G which is to be introduced into the interior I of the container in the direction of the arrow K in FIG. 7. After the article has been introduced into the container, the two tongues or flaps 52, 53 are tilted into their starting position in which they approximately close the formed filling opening E.

The folding-up of the cut of the blank 1 from the position of FIGS. 1 and 2 to an intended container, and the closing of the container for placing the container into the waste transport is effected in the following manner: After the edges 6, 7 of the blank have been compressed in the direction of the arrows F, P, as it has been described above and the pulling of the bottom caused thereby into the position of FIG. 3, the extension 29 with the flap-shaped strip 31 is folded into the interior of the container through the intermediate positions 29', 29", 29'". The strip 31 passes into its position 31'. Thereupon the two extensions 24, 25 of the parts 2, 4 according to FIG. 6 are folded along the arrows S, T into the position 24' and 25' whereupon the extension 42 of part 5 is in the direction of the arrow L moved into the position 42" (FIG. 7). In this connection, the strip 44 which as will be evident from FIG. 2, comprises lateral bevels 60, 61 is past the cut-outs 26, 27 inserted into the interior of the container.

In this position of the parts, the container is ready to be used which means the articles or waste to be inserted into the container can be inserted into the container in the direction of the arrow K. If one of these containers falls over, the flaps or tongues 52, 53 prevent the interior of the container from falling out.

If the filled container is to be inserted into a transport sack of paper or synthetic material, not only articles of waste are to be prevented from falling out of the interior of the container, but also pointed or sharp edges and infectious parts of said articles are prevented from projecting outwardly through the cut-out 46 and the opening formed by the flaps or tongues 52, 53, whereby not only the transporting means is damaged but also persons may suffer injuries.

To this end, the perforations 33, 38 are torn open, to which end the tongues 39 are grasped at the semi-circular cut-out 40, and perforation 38 is detached so that the tongue 39 occupies the position 39' in FIG. 8. When further pulling the tongue 39 in the direction of the arrow M, also the perforation 33 is detached at the areas in sections 34–36 so that the part 65 (FIG. 1) surrounded by the perforation can be folded about the edge 28 through the position 65' into the position 65". The tongue 39 can in this connection through a slot 66 provided in the central portion of edge 41 be inserted into the interior of the container and parallel to part 5 which forms a side wall of the container. The container is now closed also at its opening formed by the cut 46 so that the contents of the container can neither project nor pass outwardly. To this end, the part 65 forms the closure flap for the insert opening formed by the cut 46.

Figure 10:
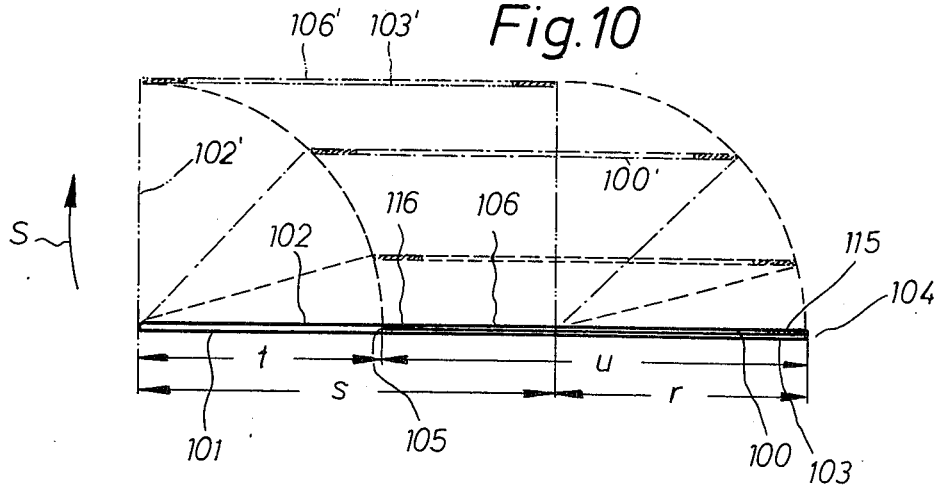
FIG. 10 represents a section taken along the line X—X of FIG. 9 and also shows the folding-up of the blank to a rhombic structure.

With the embodiment of FIGS. 9–12, the blank 1 as shown in FIG. 10, comprises a section 100 having the width r and length l of the container which after folding up the bottom 150 forms the container. Furthermore, the blank comprises a further section 101 of the same length and width s which after folding up forms one side wall 151 of the container. Adjacent thereto there is provided a section 102 which partially rests on said section 101, and has the width 5. The section 102 forms the cover part 152 with the inlet opening 114 between the flaps 113, whereas the section 103 having the width u forms the second side wall 153 of the container and extends from the 180° folding edge 104 up to the edge 105 of the section 102. Placed on this section 103 as extension of the section 102 is the fifth section 106 and, as will be described further below, is over the strip-shaped regions 115, 116 partially or entirely glued to the section 103. The walls 100, 102, 103 and 106 are moved from their positions shown in FIGS. 9 and 10 in solid line into their final folded-up position 100', 102', 103' and 106' in which the blank sections occupy their position at a right angle to their neighboring section. For purposes of use, the thus formed rhombic hollow body is tilted by 90° in the direction of the arrow S so that the container rests on the section 100, while the section 102 represents the cover part of the container, and the sections 101 and 103, 106 form the side walls of the container.

The walls 100–103 are through the intervention of the lateral fold lines 107, 108 which form the confining lines at the end of the container, provided with extensions 109, 110 which are folded about the fold lines 107, 108 in such a way that as a result thereof the transverse walls of the container are formed. The manner of forming these transverse walls is well known in the art.

The section 102 of the blank forming the container cover 152 has flaps 113 which are formed by a double-T cut 111 (FIG. 11). These flaps 113 are foldable about the lines 112 into the interior of the container and permit deformation of the inlet opening 114 (FIG. 12).

The wall 103 and the wall 106 are on regions 115 and 116 which extend from the lateral folding lines 107 to the folding line 108 glued to each other while the region 116 has the width W, and the region 115 may have the width of the same size. The gluing of the region 115 is interrupted in the central portion of said region 115. While the gluing region 116 is by the horizontal folding edge 117 limited in upward direction, the gluing region 115 is upwardly limited by a perforation 118 which for forming the tongue 119 ends in an angled-off perforated section. The tongue 119 may comprise a semi-circular recess 121 which facilitates the tearing off of the perforated sections 118 when, as shown in FIG. 12, that portion which is in downward direction confined by the perforation 118 and which forms the closure flap 124 is folded about the lower confining edge 125 of the gluing section 116 and is folded with its folding line 126 about the upper folding edge 117 in the direction of the arrow P in FIG. 12. Prior to placing the closure flap 124 upon the cover part 152 for closing the opening 114, the tongue 119 is bent and passed into the slot 122. Slot 122 is provided at the marginal edge 123 of the cover part and has about the length of the tongue 119.

Also from the embodiment of FIGS. 9–12, it will be evident that one side wall of the container likewise has a double position from which one part of the outer portion (cut section 106) is detached from its inner position (cut position 103) and is folded onto the upper cover portion 152 of the container in such a way that as a result thereof safe closure of the filling opening 114 is formed. The advantage of this embodiment is seen in the fact that the manufacture of the blank according to FIGS. 9 and 10 is relatively simple and in principle is created by two superimposed walls 103, 106 which at their longitudinal margins are connected within the regions 115, 116 entirely or partially. Inasmuch as the forms of containers from cardboard or synthetic material by folds of five sections of the blank and four folding edges is known, these parts are not claimed as novel per se but in combination with the perforation of the blue-free tongue and of the further features of the claims.

Figure 13:
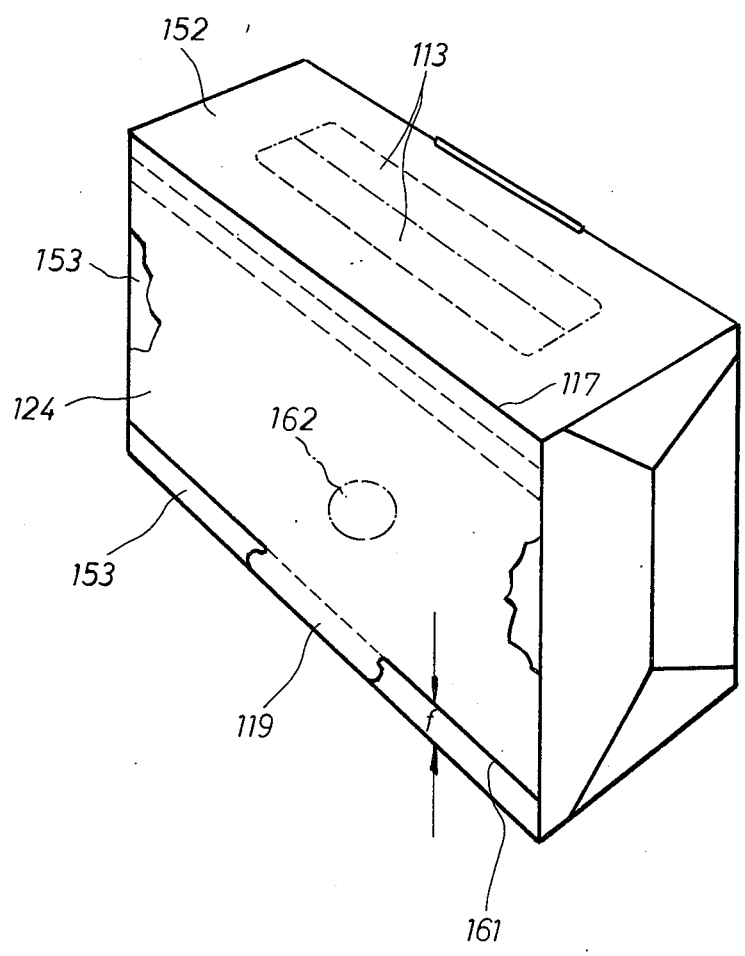
FIG. 13 illustrates still another embodiment of a container according to the invention.

The embodiment of FIG. 13 substantially corresponds to that of FIGS. 10–12. However, the lower section of the closure flap 124 has no perforation which has to be torn open for purposes of folding the flap about the edge 117. The lower edge 160 of the flap rather than ends at a distance f from the adjacent bottom edge 161, while the flap 124 is easily detachably connected to the side wall 152 of the container by means of a glued area. Also, with this design, the tongue 119 is adapted to be introduced into the slot 122, when the closure flap 124 rests upon the upper container wall 153.

It is, of course, to be understood that the present invention is, by no means, limited to the specific showing in the drawings, but also comprises any modifications within the scope of the appended claims.

What we claim is:

1. A disposable container which is adapted from a primarily double-layer collapsed and substantially flat condition to be folded up into its form of use as a safely closed receptacle for medical articles free of danger of pointed, sharp and contaminated parts of articles otherwise projecting therefrom, which includes in combination: a first wall adapted in condition of use of said container to form the longitudinal top wall of said container, said first wall having an insert opening, side walls of which one comprises two layers respectively forming an outer layer and an inner layer, said outer layer included as a fifth sidewall at least with one section as a closure flap serving as an additional cover for insert opening when the container is full and being foldable about a longitudinal edge onto said longitudinal top container wall, said insert opening extending over a portion of the container length and symmetrically to the edges of the upper longitudinal container wall.

2. A container in combination according to claim 1, in which that one of said closure flaps which is foldable onto said top container wall has a width at least approximately corresponding to the width of said longitudinal wall and is provided with an insert tongue insertable into a corresponding slot provided in said top longitudinal container wall.

3. A container in combination according to claim 1, in which said closure flap has its lower edge defined by a perforation adapted to be torn open, said perforation extending in spaced relationship to and above the lower edge of said container side wall.

4. A container according to claim 3, in which said container has vertical lateral arms, and in which said perforation extends into said vertical lateral arms, said lateral arms being spaced from the transverse edges of the pertaining container side wall and extend up to the upper folding edge of said container side wall.

5. A container according to claim 1, which comprises a bottom formed by extensions of said container side walls which extensions are adapted to be folded into the plane of said bottom, and which also comprises a container cover forming the upper longitudinal wall and including an extension projecting beyond the upper longitudinal container edge, the inner one of the two layers of one of said side walls likewise being formed by an extension pivotable about a corresponding upper longitudinal container edge into the interior of said container.

6. A container according to claim 5, in which said extension which is pivotable about a corresponding upper longitudinal container edge into the interior of said container has substantially the length and height of said container and at its lower end provided with a strip resting on said container bottom.

7. A container according to claim 1, which includes transverse walls formed by extensions of the longitudinal container walls, which extensions are foldable into the plane of said transverse walls, said extensions being adapted while partially overlapping each other to maintain their respective position, said two layers of one lateral wall being connected to each other at their upper and lower edges, and the adjacent edges of said interconnected regions defining the upper and lower borders of said closure flaps.

8. A container according to claim 1, which in collapsed condition comprises a substantially rectangular piece of foldable non-metallic material which is folded along four parallel longitudinal folding lines spaced from each other by a distance substantially equalling the width of the longitudinal walls of said container, the two end sections of said longitudinal edges overlap each other along the width of said two-layer side wall of said container.

9. A container according to claim 5, in which the two layers of one of said side walls are glued to each other at their upper and lower edge in sections of from 8 to 30 mm width while the lower glued region has substantially the width of said closure flap, said closure flap having a lateral edge connected by an extension of said perforation to the adjacent glued region.

10. A container according to claim 9, in which the upper edge of said closure flap has a folding line the width of which substantially equals the width of the upper glued region, said closure flap being foldable about said last mentioned folding line.

11. A container according to claim 1, in which said closure flap is detachably connected to one side wall of said container.

12. A container according to claim 11, in which the lower edge of said closure flap is located in spaced relationship to the adjacent bottom edge of said container.

* * * * *